United States Patent [19]

Yokota et al.

[11] Patent Number: 5,541,305
[45] Date of Patent: Jul. 30, 1996

[54] COMPOSITION COMPATIBLE WITH BLOOD

[75] Inventors: Hideyuki Yokota; Masakazu Tanaka, both of Ohtsu, Japan

[73] Assignee: Toyo Boseki Kabushiki Kaisha, Japan

[21] Appl. No.: 412,513

[22] Filed: Mar. 29, 1995

Related U.S. Application Data

[63] Continuation of Ser. No. 820,515, Jan. 14, 1992, abandoned.

[30] Foreign Application Priority Data

Jan. 16, 1991 [JP] Japan .................................. 3-017136
May 20, 1991 [JP] Japan .................................. 3-145528

[51] Int. Cl.$^6$ .......................... A61K 31/725; C08B 37/10
[52] U.S. Cl. ........................ 536/21; 536/112; 536/122; 523/112
[58] Field of Search ................... 514/54, 56; 523/112; 536/21, 112, 122

[56] References Cited

U.S. PATENT DOCUMENTS

| | | | |
|---|---|---|---|
| 3,755,218 | 8/1973 | Yen et al. | 428/35.5 |
| 4,118,485 | 10/1978 | Eriksson et al. | 514/56 |
| 4,613,665 | 9/1986 | Larm | 536/20 |
| 4,654,327 | 3/1987 | Teng | 514/56 |
| 4,720,512 | 1/1988 | Hu et al. | 523/112 |
| 4,871,357 | 10/1989 | Hsu et al. | 604/266 |
| 5,069,899 | 12/1991 | Whitbourne et al. | 424/56 |
| 5,128,408 | 7/1992 | Tanaka et al. | 525/54.2 |
| 5,159,050 | 10/1992 | Onwumere | 528/67 |
| 5,159,051 | 10/1992 | Onwumere et al. | 528/67 |

FOREIGN PATENT DOCUMENTS

| | | |
|---|---|---|
| 0338418 | 10/1989 | European Pat. Off. . |
| 2364939 | 9/1976 | France . |
| 2610698 | 9/1976 | Germany . |
| 49-38945 | 4/1974 | Japan . |
| 52-36779 | 9/1977 | Japan . |
| 52-36777 | 9/1977 | Japan . |
| 58-92363 | 6/1983 | Japan . |
| 1-131226 | 5/1989 | Japan . |

OTHER PUBLICATIONS

Jpn. Kokai Tokkyo Koho Chem. Ab. 96(24): 205450a (1982).
Masuhara et al; Chem. Ab, 81:82408y (1974).
Toray; Chem. Ab. 94:77556n (1981).
Toray; Chem. Ab. 96:223331s (1982).
Langer et al (Eds); Med. Appl. Controlled Rel. vol. II pp. 77–106 (1984).
Imanishi et al; Chem. Ab. 104:155913q (1986).
Terumo; Chem. Ab. 97:11884v (1982).
Hu et al; Chem. Ab. 112:42675k (1990).
Cohn et al; Chem Ab. 115:78965f (1991).

*Primary Examiner*—Gary L. Kunz
*Assistant Examiner*—Kathleen Kahler Fonda
*Attorney, Agent, or Firm*—Leydig, Voit & Mayer, Ltd.

[57] ABSTRACT

A material compatible with blood obtained by heparinizing a polymer having quarternary ammonium groups with an alkali metal salt or an alkaline earth metal salt of heparin or the analog by ion exchange is provided. The equivalent ratio (M/S) of alkali metal atoms or alkaline earth metal atoms (M) in the heparin or the analog bonded to the polymer to sulfur atoms (S) in heparin or the analog bonded to the polymer is 0.4 or less.

21 Claims, No Drawings

1

COMPOSITION COMPATIBLE WITH BLOOD

This is a continuation of application Ser. No. 07/820,515 filed on Jan. 14, 1992, now abandoned.

BACKGROUND OF THE INVENTION

1. Field of the Invention

The present invention relates to a material compatible with blood for medical use, which is brought into contact with an organism or a vital component, and more particularly to a material compatible with blood which has satisfactory anti-blood-clotting and mechanical properties.

2. Description of the Prior Art

In recent years, polymer materials excellent in moldability, elasticity, flexibility, and the like have been widely used as materials for medical use. Particularly, polymer materials of this type have been expected to be used in greater amounts as disposable containers such as an injection case, a blood bag, and a heart catheter, as well as artificial organs such as an artificial kidney, an artificial lung, an auxiliary circulating unit, and as artificial blood vessels. When the materials are used for medical purposes, various kinds of reactions that may compromise the vitality and/or viability of an organism may occur. In the case of blood, for example, a compatibility with blood is required. Anti-coagulation polymer materials provided hitherto can be obtained by the following three methods: (1) bonding heparin or an analog thereof to the surface of the polymer material; (2) applying a negative charge to the surface of the polymer material; and (3) making the surface of the polymer material inactive. The material of the present invention is obtained by (1). Method (1) is divided into three categories: (A) blending the polymer material with heparin or an analog thereof; (B) ion-bonding heparin or an analog thereof to a cationic group in the polymer material; and (C) covalent bonding heparin or an analog thereof to the polymer material. However, in anti-blood-clotting polymer materials obtained in Methods (A) and (B), heparin or the analog is detached from the surface of the polymer material when used over a long period of time under physiological conditions, so that these materials are inappropriate as medical materials which are used by being fixed in vivo. In contrast, in materials compatible with blood obtained in Method (C), heparin or the analog thereof is covalently bonded to the polymer material, so that these materials have an advantage in that heparin or the analog are not likely to be detached from the material. However, according to the conventional covalent bond, conformational changes are given to D-glucosamine and D-glucuronic acid which is heparin components, so that the compatibility with blood are minimized.

SUMMARY OF THE INVENTION

The material compatible with blood of this invention, which overcomes the above-discussed and numerous other disadvantages and deficiencies of the prior art, is obtained by heparinizing a polymer having quaternary ammonium groups with an alkali metal salt or an alkaline earth metal salt of heparin or an analog thereof by ion exchange, the polymer being obtained by quaternizing tertiary amino groups of a polymer with a quaternizing agent, wherein the equivalent ratio of alkali metal atoms or alkaline earth metal atoms (M) in heparin or the analog thereof bonded to the polymer to sulfur atoms (S) in heparin or an analog thereof bonded to the polymer (M/S) is 0.5 or less.

In a preferred embodiment, the polymer having quaternary ammonium groups is a polyurethane or a polyurethaneurea having quaternary ammonium groups obtained by quaternizing tertiary amino groups of a polyurethane or a polyurethaneurea with a quaternizing agent; the polyurethane or the polyurethaneurea contains as its main components a polyaminoetherpolyol, a compound having at least two functional groups capable of reacting with isocyanato groups, and a polyisocyanate; and the polyaminoetherpolyol is obtained by condensation of diols and contains at least 30 mol% amino alcohol represented by the general formula (I):

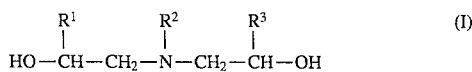

wherein $R^1$ and $R^3$ are independently alkyl groups with 1 to 5 carbon atoms, and $R^2$ is an alkyl group, an aralkyl group, or an aryl group with 1 to 15 carbon atoms.

In a preferred embodiment, the polymer having quaternary ammonium groups is a polyurethane or a polyurethaneurea having quaternary ammonium groups obtained by quaternizing at least a part of the tertiary amino groups in a polyurethane or a polyurethaneurea with an alkyl halide or an active ester, wherein the polyurethane or the polyurethaneurea contains as its main components a diisocyanate, a polysiloxane having a hydroxyl group or an amino group at, at least, one of its molecular termini, and a polyaminoetherpolyol having tertiary amino groups.

In a preferred embodiment, the polymer having quaternary ammonium groups contains as its component polytetramethylene glycol.

In a preferred embodiment, the total of the number of carbon atoms of the two side chains bonded to quaternary nitrogen atoms of the polymer having quaternary ammonium groups is 5 to 16, in which one side chain is bonded to the tertiary nitrogen atom of the polymer having tertiary amino groups and the other side chain is derived from the quaternizing agent.

In a preferred embodiment, the coefficient of water absorption of the polymer having quaternary ammonium groups is 6% by weight or less.

In a preferred embodiment, the heparinization is carried out in a mixed solvent of water-soluble organic solvent and water.

Thus, the invention described herein makes possible the objective of (1) providing a material compatible with blood which can maintain excellent compatibility with blood for a long period of time.

DESCRIPTION OF THE PREFERRED EMBODIMENTS

The present invention will be described in detail below.

The material compatible with blood of the present invention is a material obtained by heparinizing a polymer having quaternary ammonium groups with an alkali metal salt or an alkaline earth metal salt of heparin or an analog thereof.

The polymer having quaternary ammonium groups is a polymer in which tertiary amino groups of a polymer having tertiary amino groups are quaternized. The polymer is preferably polyurethane or polyurethaneurea. The polyurethane or polyurethaneurea contains as its main components a polyaminoetherpolyol, a compound having at least two functional groups capable of reacting with isocyanato groups, and a polyisocyanate.

The polyaminoetherpolyol is a polyetherpolyol having tertiary amino groups, and preferably contains as its diol component an amino alcohol represented by the following general formula (I).

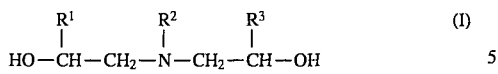

In the general formula (I), examples of the alkyl groups with 1 to 5 carbon atoms represented by $R^1$ and $R^3$ include saturated lower alkyl groups such as methyl, ethyl, propyl, isopropyl, butyl, isobutyl, tertiary butyl, pentyl, and isopentyl. Examples of alkyl groups with 1 to 15 carbon atoms represented by $R^2$ include the above saturated lower alkyl groups; chain or branch alkyl groups such as hexyl, heptyl, octyl, nonyl, decyl, undecyl, dodecyl, tridecyl, tetradecyl, and pentadecyl; and saturated cycloalkyl groups such as cyclopentyl, cyclohexyl, and cycloheptyl. Examples of the aralkyl group represented by $R^2$ include benzyl and phenetyl, and these groups can be substituted with alkyl groups such as methyl, ethyl, and propyl. Examples of the aryl group represented by $R^2$ include phenyl and naphthyl, and these groups can be substituted with alkyl groups such as methyl, ethyl, and propyl. Among them, the alkyl groups with 1 to 15 carbon atoms are preferred.

Examples of the tertiary amino alcohol represented by the general formula (I) include 3-methyl- 3-aza-1,5-pentanediol, 3-ethyl-3-aza-1,5-pentanediol, 3-propyl-3-aza-1,5-pentanediol, 3-isobutyl-3-aza-1,5-pentanediol, 3-n-pentyl-3-aza-1,5-pentanediol, 3-n-hexyl- 3-aza-1,5-pentanediol, 3-cyclohexyl-3-aza-1,5pentanediol, 3-phenyl-3-aza-1,5-pentanediol, 3-benzyl- 3-aza-1,5-pentanediol, 4-methyl-4-aza-2,6-heptanediol, 4-ethyl-4-aza-2,6-heptanediol, 4-n-propyl-4-aza-2,6-heptanediol, 4-isopropyl-4-aza-2,6-heptanediol, 4-n-butyl- 4-aza-2,6-heptanediol, 4-isobutyl-4-aza-2,6-heptanediol, 4-hexyl-4-aza-2,6-heptanediol, 4-cyclo-hexyl- 4-aza-2,6-heptanediol, 4-benzyl-4-aza-2,6-heptanediol, 4-phenyl-4-aza-2,6-heptanediol, and 4-n-lauryl- 4-aza-2,6-heptanediol The polyaminoetherpolyol can contain as its diol component a compound represented by the following general formula (II) or (III) in addition to the amino alcohol represented by the general formula (I).

wherein $R^4$ is an alkylene group with 2 to 20 carbon atoms, $R^5$ is an alkylene group with 2 to 5 carbon atoms, and m is an integer of 2 or more.

Examples of the diol represented by the general formula (II) include alkylene glycols such as ethylene glycol, propylene glycol, tetramethylene glycol, 1,6-hexanediol, and neopentyl glycol. Examples of the diol represented by the general formula (III) include diethylene glycol, triethylene glycol, polyethylene glycol having a molecular weight of 200 to 2,000, dipropylene glycol, tripropylene glycol, polypropylene glycol having a molecular weight of 200 to 1,000, polytetramethylene glycol having a molecular weight of 200 to 1,000, and polyhexamethylene glycol having a molecular weight of 200 to 1,000.

The polyaminoetherpolyol preferably contains at least 30 mol% amino alcohol represented by the general formula (I). When the content of the amino alcohol is less than 30 mol%, the content of the tertiary amino groups in the polyurethane or polyurethaneurea is decreased, resulting in the decrease in the amount of heparin or the analog which is bonded when the polyurethane or polyurethaneurea is heparinized. Thus, a material having a satisfactory blood compatibility cannot be obtained.

The polyaminoetherpolyol preferably has a molecular weight of 200 to 8,000, and more preferably 500 to 4,000. The content of nitrogen atoms of tertiary amino groups in the polyaminoetherpolyol is preferably 1.1 to 10.0 mmol/g, and more preferably 1.5 to 7.8 mmol/g.

Moreover, polyaminoetherpolyol is contained in the polyurethane or the polyurethaneurea so that the tertiary amino groups present in the molecules of the polyaminoetherpolyol are contained in the polyurethane molecule or the polyurethaneurea molecule preferably in an amount of 0.05 to 5.00 mmol/g, and more preferably 0.1 to 3.0 mmol/g. Moreover, the polyaminoetherpolyol is contained in polyurethane or polyurethaneurea preferably in an amount of 1 to 90% by weight, and more preferably 5 to 70% by weight.

Examples of the compound having at least two functional groups capable of reacting with isocyanato groups, which is a component of the polyurethane or the polyurethaneurea, include a polysiloxane or a polyoxyalkylene having a hydroxyl group or an amino group at, at least, one of its molecular termini, a poly esterdiol, and a polylactonediol. Among them, the polysiloxane or the polyoxyalkylene having a hydroxyl group or an amino group at both termini is preferred. These compounds form a soft segment in the polyurethane or the polyurethaneurea. The polysiloxane having a hydroxyl group or an amino group at both termini is preferably represented by the following general formula (IV):

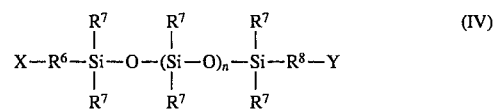

wherein X and Y are independently —O, —$NH_2$, or substituted amino groups having 2 to 10 carbon atoms; $R^6$ and $R^8$ are independently an alkylene group, an oxyalkylene group, an aralkylene group, or an arylene group having 2 to 10 carbon atoms; $R^7$ is an alkyl group, an aryl group or an aralkyl group having 1 to 10 carbon atoms; and n is an integer of 5 to 300.

The molecular weight of the polysiloxane represented by the general formula (IV) is preferably 200 to 20,000, more preferably 500 to 8,000, and most preferably 1,000 to 4,000. The content of the polysiloxane represented by the general formula (IV) in the resulting polyurethane or the polyurethaneurea is preferably 20 to 95% by weight, and more preferably 30 to 85% by weight.

Examples of the polyoxyalkylene having a hydroxyl group or an amino group at both termini include polyethylene glycol, polypropylene glycol, polytetramethylene glycol, or copolymers thereof. Among them, polytetramethylene glycol is preferred. The molecular weight of the polyoxyalkylene having a hydroxyl group or an amino group at both termini is preferably 200 to 20,000, more preferably 500 to 8,000, and most preferably 1,000 to 4,000. The content of the polyoxyalkylene in the resulting polyurethane or the polyurethaneurea is preferably 20 to 95% by weight, and more preferably 30 to 85% by weight.

The polyesterdiol can be obtained by the reaction between diols and dicarboxylic acids or ester-forming derivatives. The diols preferably have 2 to 15 carbon atoms. Examples of the diols include ethylene glycol, propylene glycol, tetramethylene glycol, pentamethylene glycol, 2,2-dimethyltrimethylene glycol, hexamethylene glycol, decamethylene glycol, 1,4-dihydroxycyclohexane, and 1,4-dihydroxymethylcyclohexane. Examples of the dicarboxylic acids or ester-forming derivatives include aliphatic dicarboxylic acids such as cebacic acid, adipic acid, dodecanedicarboxylic acid, glutaric acid, succinic acid malonic acid, oxalic acid, and azeliac acid; aromatic dicarboxylic acids such as terephthalic acid and isophthalic acid; or halides thereof, active esters thereof, and amides thereof.

Examples of the polylactonediol include polylactonediol obtained by the ring-opening polymerization of ε-caprolactone, etc.

As the polyisocyanate, all of the polyisocyanates used for producing conventional polyurethane and polyisocyanates which will be developed in the future can be used. Among them, diisocyanates are preferred. Examples of diisocyanates include ethylene diisocyanates, trimethylene diisocyanate, tetramethylene diisocyanate, pentamethylene diisocyanate, octamethylene diisocyanate, undecamethylene diisocyanate, dodecamethylene diisocyanate, 3,3'-diisocyanatopropylether, cyclopentane-1,3-diisocyanate, cyclohexane-1,4-diisocyanate, 2,4-tolylene diisocyanate, 2,6-tolylene diisocyanate, a mixture of 2,4-tolylene diisocyanate and 2,6-tolylene diisocyanate, xylylene-1,4-diisocyanate, xylylene-1,3-diisocyanate, 4,4-diphenylmethane diisocyanate, 4,4-diphenylpropane diisocyanate, 4-isocyanatobenzyl isocyanate, m-phenylene diisocyanate, p-phenylene diisocyanate, naphthalene-1,4-diisocyanate, and naphthalene-1,5-diisocyanate.

The polyurethane or polyurethaneurea can contain, if necessary, other components having functional groups capable of reacting with isocyanato groups. Examples of these components include low molecular weight polyamines, low molecular weight polyols, and low molecular weight amino alcohols. These compounds extend a chain of the polyurethane or polyurethaneurea. All of the known and novel compounds can be applicable. Among polyols, diols are preferred. As for diols, examples include ethylene glycol, propylene glycol, tetramethylene glycol, 1,5-heptanediol, 1,6-hexanediol, 1,10-decanediol, 1,4-dihydroxycyclohexane, 1,4-dihydroxymethylcyclohexane, diethylene glycol, and triethylene glycol. Among polyamines, diamines are preferred. As for diamines, examples include ethylene diamine, propylene diamine, butylene diamine, hexamethylene diamine, xylylene diamine, phenylene diamine, and 4,4'-diaminodiphenylmethane. In addition to these, diamines in a broad sense such as hydrazine and dihydrazine of dicarboxylic acid (such as oxalic dihydrazide, succinic dihydrazide, adipic dihydrazide, cebacic dihydrazide, and isophthalic di-hydrazide) can be used. Examples of the amino alcohol include methanolamine, 2-aminoethanol, 3-aminopropanol, and 4-aminobutanol.

The polyaminoetherpolyol can be produced as follows. First, an amino acid represented by the general formula (I) or a mixture including the amino alcohol and a diol represented by the general formula (II) or (III) and other diols is provided and then a catalyst such as phosphorous acid is added. The resulting mixture of the amino alcohol or the amino alcohol and diol, and the catalyst is heated to a temperature in the range of 150° to 270° C. under ordinary pressure, and preferably 200° to 250° C. The mixture is allowed to react for 1 to 30 hours and preferably for 3 to 20 hours while distilling off generated water, and then evacuated to 10 mmHg or less, preferably 3 mmHg or less over 0.5 to 6 hours, preferably 1 to 4 hours. The mixture is allowed to react for 1 to 10 hours under the above-mentioned pressure and temperature, preferably 2 to 7 hours, thereby obtaining the polyaminoetherpolyol.

A production method of the polyurethane or polyurethaneurea is not particularly limited. For example, it can be produced as follows. The polyaminoetherpolyol, the compound having at least two functional groups capable of reacting with isocyanato groups, and the polyisocyanate are reacted to obtain a prepolymer having isocyanato groups at both terminals. It is preferred that this prepolymer is obtained by reacting each of the materials so that the molar ratio of isocyanato group to hydroxyl group is 1.1 to 5.0 (preferably 1.5 to 3.0). This prepolymer is reacted with a low molecular weight compound having at least two functional groups capable of reacting with the isocyanato groups such as the above-mentioned low molecular weight diols, diamines, and amino alcohols to extend a molecular chain of the prepolymer, thereby obtaining polyurethane or polyurethaneurea. The content of tertiary amino groups contained in the resulting polyurethane or polyurethaneurea is preferably 0.05 to 5.0 mmol/g, more preferably 0.1 to 3.0 mmol/g, and most preferably 0.2 to 2.0 mmol/g.

The polymer having quaternary ammonium groups used in the present invention is a polymer obtained by quaternizing tertiary amino groups of a polymer having tertiary amino groups with a quaternizing agent. Examples of the quaternizing agent include alkyl halides, cycloalkyl halides, and active esters. Among them, alkyl halides and active esters are preferred, more preferably alkyl halides having 1 to 10 carbon atoms, and most preferably alkyl halides having 2 to 8 carbon atoms. These quaternizing agents can be used in combination of two or more kinds.

The total of the number of carbon atoms of the two side chains bonded to the quaternary nitrogen atom of the polymer having quaternary ammonium groups is preferably 5 to 16, and more preferably 6 to 14. One side chain is bonded to the tertiary nitrogen atom of the polymer having tertiary amino groups and the other side chain is derived from the quaternizing agent. When the polymer having quaternary ammonium groups is polyurethane or polyurethaneurea in which tertiary amino groups are quaternized, and the quaternizing agent is an alkyl halide, the total of the number of carbon atoms of $R^2$ of the amino alcohol represented by the general formula (I) and the number of carbon atoms of the alkyl group derived from the quaternizing agent is preferably 5 to 16, and more preferably 6 to 14.

When the total number of the carbon atoms is 4 or less, the coefficient of water absorption of the resulting polymer having quaternary ammonium groups exceeds 10%, so that, in the resulting material compatible with blood, heparin or an analog thereof tends to be rapidly detached from the polymer having quaternary ammonium groups. Therefore, the compatibility with blood cannot be maintained for a long period of time, and mechanical strength of the material compatible with blood tends to be decreased, causing problems for practical use. In contrast, when the total number of the carbon atoms is 17 or more, because of increased steric hindrance between the tertiary amino groups of the polymer and the quaternizing agent, the degree of quaternization cannot be improved. Therefore, the amount of heparin or an analog thereof bonded to the resulting polymer having quaternary ammonium groups tends to be decreased, and compatibility with blood tends to be difficult.

The degree of quaternization of the tertiary amino groups is preferably 10% or more, more preferably 20% or more, and most preferably 30% or more.

It is preferred that the coefficient of water absorption of the polymer having quaternary ammonium groups is 6% by weight or less. When the coefficient of water absorption of the polymer exceeds 6% by weight, in the resulting material compatible with blood, heparin or an analog thereof is rapidly eluted from the polymer, so that the compatibility with blood cannot be maintained for a long period of time.

The quaternization can be effected before or after the molding of polyurethane or polyurethaneurea. If the tertiary amino groups is quaternized before the molding of polyurethane or polyurethaneurea, it is done in a solvent such as dimethylformamide, etc., and if quaternized after the molding of polyurethane or polyurethaneurea, it can be done without a solvent respectively from room temperature to its boiling point.

The quaternizing agent can be preferably used in the proportion of 0.1 to 10.0 moles, and more preferably 0.5 to 5.0 moles per mole of tertiary amino groups in the polymer.

Finally, the material compatible with blood of the present invention is obtained by heparinizing the polymer in which the tertiary amino groups are quaternized with an alkali metal salt or an alkaline earth metal salt of heparin or an analog thereof. The alkali metal salt of heparin or the analog thereof is preferably sodium salt or potassium salt of heparin or the analog thereof, and the alkaline earth metal salt of heparin or the analog thereof is preferably magnesium salt or calcium salt of heparin or the analog thereof.

The heparinization can be effected by the following reaction system:

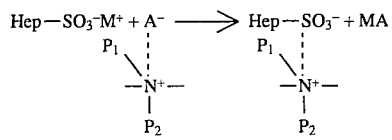

In the above reaction system, Hep-SO$_3$M is heparin or the analog, P$_1$ and P$_2$ are side chains bonded to the quaternary nitrogen atom of the polymer having quaternary ammonium groups, in which P$_1$ is the side chain bonded to the tertiary nitrogen atom of the polymer having tertiary amino groups, and P$_2$ is a group derived from the quaternizing agent, A$^-$ is a counterion derived from the quaternizing agent, and M$^+$ is an alkali metal ion or an alkaline earth metal ion.

Hep-SO$_3^-$ is substituted for A$^-$, an anion of the polymer having quaternary ammonium groups, and is bonded to the polymer by the ionic bond. At this time, M$^+$, a cation of Hep-SO$_3^-$, are bonded to A$^-$ and become free. Thus, as the number of bonding sites between the heparin and the polymer becomes greater, an M/S equivalent ratio becomes smaller and the bond between heparin or an analog thereof and the polymer becomes stronger, wherein M/A is an equivalent ratio of an alkali metal atoms or alkaline earth metal atoms (M) in heparin or the analog thereof bonded to the polymer to sulfur atoms (S) in heparin or the analog thereof bonded to the polymer. Sulfur atoms are present in sulfate groups (—OSO$_3$M) or sulfamino groups (—NHSO$_3$M) in heparin or the analog thereof. When M is an alkali metal atom, the M/S equivalent ratio is the molar ratio of alkali metal atoms in heparin or the analog thereof bonded to the polymer to sulfur atoms in heparin or the analog thereof bonded to the polymer. When M is an alkaline earth metal atom, the M/S equivalent ratio is two times the molar ratio of alkaline earth metal atoms in heparin or the analog thereof bonded to the polymer to sulfur atoms in heparin or the analog thereof bonded to the polymer. Therefore, M/S is an equivalent ratio of the number of the sulfate groups and the sulfamino groups in heparin or an analog thereof which are not ion-bonded to the polymer having quaternary ammonium groups to the total number of the sulfate groups and the sulfamino groups in heparin or the analog thereof.

The material obtained in the present invention is characterized in that the M/S equivalent ratio of the material obtained in the present invention is 0.5 or less, and preferably 0.4 or less. The bond between heparin or an analog thereof and the polymer can become appropriately strong by limiting the M/S equivalent ratio in this range, the detachment of heparin or the analog thereof from the polymer in vivo can be controlled, and the material can be used as a material compatible with blood for a long period of time.

The heparinization can be effected before and after the molding of the polymer having quaternary ammonium groups. It is preferred that the heparinization is effected by immersing a mold of the polymer having quaternary ammonium groups into a solution of heparin or an analog thereof described below. This solution, usually having a concentration of 0.1 to 10%, and preferably 0.5 to 5%, can be used. Although the reaction can proceed at room temperature, it is more preferable that the reaction is effected by heating to a temperature in the range of about 40° to 100° C. Examples of heparin or an analog thereof used include derivatives such as heparin, heparin metal salt, 4-heparin, and 4-heparin metal salt; heparinoids such as chondroitin sulfate and dextran sulfate; and heparin or the analogues such as PVA sulfate.

As the solvent used for the heparinization, a mixed solvent of water and water-soluble organic solvents, such as acetone, ethanol, tetrahydrofuran, dimethylformamide, or dimethylacetamide can be used.

Among them, a mixed solvent of water with tetrahydrofuran, dimethylacetamide, or dimethylformamide is preferred. In order to realize the M/S equivalent ratio of 0.5 or less, which is the characteristic of the present invention, the mixed solvent of water with tetrahydrofuran is most preferable.

A mixed ratio of water to the organic solvent is 20/1 to 3/7 in a volume ratio, and preferably 10/1 to 3/5.

In the material compatible with blood of the present invention, the amount of heparin bonded to the polymer having quaternary ammonium groups is great, so that excellent compatibility with blood can be maintained for a long period of time.

As general problems which arise when the polymer material is used being in contact with blood, harmful effects caused by the elution of additives (plasticizers, stabilizers, polymerization catalysts, etc.) and unreacted substances (monomers, oligomers, etc.) of the material should be taken into consideration in addition to the compatibility with blood. In the material compatible with blood of the present invention, it is not required that the plasticizers and the like are not added. Moreover, the polymer material tends to be affected by complicated factors such as decomposition by oxidation caused by radicals and oxygen and metabolism in vivo. The material compatible with blood of the present invention contains as its main components polyurethane or polyurethaneurea, so that chemical stability is high. Thus, harmful eluted substances are hardly generated.

Furthermore, since the polyurethane or polyurethaneurea consists of a polyaminoether segment with a high hydrophilicity, in which the tertiary amino groups are quaternized, a polyether segment with a hydrophobicity, and a urethane bond or a urea bond with a crystallinity, the phase separation occurs in a solid phase and a microdomain structure is formed. This structure is similar to that of vascular inner wall. Thus, the anti-blood-clotting property can be expected from a structural point of view.

EXAMPLES

Hereinafter, the present invention will be described by way of illustrating examples. In the examples, unless specifically indicated, the term "parts" refers to "parts by weight".

Example 1

First, 1,472 parts of 4-methyl-4-aza-2, 6-heptanediol, 591 parts of 1,6-hexanediol, and 12.3 parts of phosphorous acid were charged into an autoclave. The mixture was heated and stirred at a temperature of 200° to 220° C. at atmospheric pressure under a stream of nitrogen for 26 hours and allowed to react while distilling off generated water. Then, the mixture was evacuated at 220° C. from 760mmHg to 0.3 mmHg over 2 hours and was allowed to react at 220° C. and 0.3 mmHg for another 3 hours. As described above, polyaminoetherdiol (a) having an OH value of 57.3 and containing 6.11 mmol/g of nitrogen atoms of the tertiary amino groups was obtained.

Next, 1,800 parts of polytetramethylene glycol with a number average molecular weight of 1,500, 300 parts of the polyaminoetherdiol (a), 90.1 parts of 1,4-butanediol, 0.3 parts of dibutyltin dilaurate, and 554 parts of 4,4'-diphenylmethane diisocyanate (hereinafter, referred to as MDI) were dissolved in a mixed solvent of 1,994 parts of tetrahydrofuran (hereinafter, referred to as THF) and 3,887 parts of dimethylformamide (hereinafter, referred to as DMF). The mixture was allowed to react at 40° C. under a stream of nitrogen for i hour and then at 60° C. for another 15 hours. As described above, a base polymer solution A having a solid content of 32% and a viscosity of 3,200 poises (30° C.) was obtained. To this solution, DMF was added and stirred to obtain a 5% solution. Then, 10 g of 5% solution was uniformly applied onto the surface area (100 cm$^2$) of a glass plate held horizontal, after which the resulting glass plate was dried under a stream of nitrogen at 40° C. for 1 hour and at 60° C. for 2 hours, followed by drying under reduced pressure at 60° C. for 15 hours to obtain a base polymer film $A_1$ with a thickness of 50 μm. To 100 parts of 10% base polymer solution obtained by diluting the base polymer solution A with DMF, 4.58 parts of hexyl iodide was added and allowed to react with stirring at 70° C., thereby quaternizing tertiary amino groups in the base polymer. This solution was diluted with dioxane to obtain a 5% solution. A polymer film $A_2$ having quaternary ammonium groups with a thickness of 50 μm was obtained in the same way as in the base polymer film $A_1$.

About 0.2 g of the base polymer film $A_1$, and 0.2 g of the polymer film $A_2$ having quaternary ammonium groups were carefully weighed respectively, and each of the films was dissolved in 50 ml of a mixed solvent of dioxane/ethanol (7:3 by volume), and measured for the content of tertiary amino groups by means of a potentiometer (Hiranuma Seisakusho Co.; Comtite-7). The solution of each polymer film was titrated with N/10-HClO$_4$ dioxane solution (commercially available 60% aqueous HClO$_4$ solution was diluted with dioxane so that the concentration was 0.1 normal) and the content of tertiary amino groups was calculated from the point of inflection of the titration curve. The content of tertiary amino groups of the base polymer film $A_1$ was 0.67 mmol/g, and that of the polymer film $A_2$ having quaternary ammonium groups was 0.25 mmol/g. These results showed that the degree of quaternization was about 63%.

Next, the polymer film $A_2$ having quaternary ammonium groups was treated with heparin by being immersed in a 1% solution of heparin sodium salt (THF/water=¼ by weight was used as a solvent) at 60° C. for 2 hours, thereby obtaining a heparinized polymer film $A_3$ having quaternary ammonium groups.

These resulting films were cut into circles with a diameter of 3 cm, and these samples were thoroughly rinsed with distilled water and dried by blotting up water on the film surfaces with filter paper. The film samples were affixed to the center area of watch-glasses 10 cm in diameter. On the surface of the film, 200 μl of blood plasma of rabbit (Japanese white species) to which citric acid had been added was placed, and to this, 200 μl of an aqueous solution of calcium chloride at the concentration of 1/40 M was added. The watch glasses were floated on water in a water bath at 37° C. The water was gently stirred and the time needed for coagulation of plasma to take place (i.e., until the plasma did not flow) from the time of the addition of the aqueous solution of calcium chloride was measured. The time that was needed for coagulation of plasma was divided by the standard value. The standard value was obtained by measuring the time needed for coagulation on the watch-glass without using the film samples. The results are shown in Table 1 as the relative coagulation time.

Next, the solution of the base polymer film $A_1$, and the solution of the polymer film $A_2$ having quaternary ammonium groups were respectively diluted with DMF to obtain 1% solutions. Then, glass beads of 40–60 mesh were immersed in 100 ml of the respective solutions for 30 minutes. The glass beads were filtered with a glass filter, dried at 40° C. for 3 hours under a stream of nitrogen, and dried at 60° C. for another 12 hours under reduced pressure, resulting in polymer-coated glass beads. Half volume of glass beads coated with the polymer having quaternary ammonium groups was treated by immersing in a 1% solution of heparin sodium salt (THF/water=¼ by weight was used as a solvent) at 60° C. for 2 hours, and then dried in the same way at described above. To a test tube made of plastic, 200 mg of these coated beads, 500 μl of veronal buffer, and 500 μl of serum (pooled serum from healthy persons) were added, and the mixture was incubated at 37° C. with gentle shaking for 30 minutes. Then, the amounts produced of 50% Hemolytic unit of complement (abbreviated as $CH_{50}$) and of C3a and C5a (activated fragments of complement, of which production means activation of complement) were measured. The results are shown in Table 1. For the measurement of $Ch_{50}$, the method of Meyer (M. M. Meyer, "Complement and complement fixation", in *Experimental Immune Chemistry*, 2nd Ed., p. 133, Charles C. Thomas Publisher, Stuttgart, 1964) was used, and for the measurement of c3a and C5a, radioimmunoassay kits available from the Upjohn Co. were used.

Moreover, the amounts of sulfur and sodium contained in the obtained heparinized polymer film having quaternary ammonium groups were determined by elemental analysis (ion chromatography) to obtain a content of S (% by weight) and Na/S molar ratio. The results of the above are shown in Table 1.

TABLE 1

|  |  | Relative coagulation time | Activity of complement | | | Content of S | Na/S |
|---|---|---|---|---|---|---|---|
|  |  | (Glass = 1.00) | $CH_{50}$ (%) | C3a (ng/ml) | C5a (ng/ml) | (% by weight) | Molar ratio |
| Example 1 | Base polymer Film $A_1$ | 2.90 | 94.0 | 350 | 200 | — | — |
|  | Polymer film $A_2$ having quaternary ammonium groups | 3.40 | 100 | 200 | 120 | — | — |
|  | Heparinized polymer film $A_3$ having quaternary ammonium groups | >10 | 100 | 20 | 40 | 0.975 | 0.392 |
| Example 2 | Base polymer film $B_1$ | 2.70 | 95.0 | 345 | 180 | — | — |
|  | Polymer film $B_2$ having quaternary ammonium groups | 3.05 | 99.0 | 195 | 132 | — | — |
|  | Heparinized polymer film $B_3$ having quaternary ammonium groups | >10 | 99.0 | 25 | 38 | 1.03 | 0.379 |
| Example 3 | Base polymer film $C_1$ | 2.70 | 95.0 | 345 | 180 | — | — |
|  | Polymer film $C_2$ having quaternary ammonium groups | 3.20 | 100 | 190 | 130 | — | — |
|  | Heparanized polymer film $C_3$ having quaternary ammonium groups | >10 | 100 | 20 | 40 | 1.10 | 0.370 |
| Comparative Example 1 | Base polymer film $D_1$ | 2.70 | 95.0 | 345 | 180 | — | — |
|  | Polymer film $D_2$ having quaternary ammonium groups | 3.05 | 99.0 | 195 | 132 | — | — |
|  | Heparinized polymer film $D_3$ having quaternary ammonium groups | >10 | 100 | 25 | 40 | 0.640 | 0.628 |
| Comparative Example 2 | Base polymer film $E_1$ | 2.70 | 95.0 | 345 | 180 | — | — |
|  | Polymer film $E_2$ having quaternary ammonium groups | 3.05 | 99.0 | 195 | 132 | — | — |
|  | Heparinized polymer film $E_3$ having quaternary ammonium groups | >10 | 95.0 | 20 | 40 | 0.570 | 0.623 |

Example 2

First, 8,040 parts of 3-n-butyl-3-aza-1,5-pentanediol and 10.3 parts of phosphorous acid were charged into an autoclave. The mixture was heated with stirring at a temperature of 200° to 230° C. at atmospheric pressure under a stream of nitrogen for 26 hours and allowed to react while distilling off generated water. Then, the mixture was evacuated at 230° C. from 760 mmHg to 0.3 mmHg over 2 hours and was allowed to react at 230° C. and 0.3 mmHg for another 3 hours. As described above, polyaminoetherdiol (b) having an OH value of 64.7 and containing 6.75mmol/g of nitrogen atoms of tertiary amino groups was obtained.

Next, 3,240 parts of polytetramethylene glycol. with a number average molecular weight of 1,800, 1,195 parts of MDI, 773.4 parts of the polyaminoetherdiol (b), 0.3 parts of dibutyltin dilaurate, and 191.1 parts of 1,4-butanediol were dissolved in a mixed solvent of 3,782 parts of THF and 7,564 parts of DMF. The mixture was allowed to react under a stream of nitrogen at 20° C. for 1 hour, further at 40° C. for 20 hours, thereby obtaining a base polymer solution B having a solid content of 32% and a viscosity of 1,800 poises (30° C.). This base polymer solution B was treated with hexyl iodide in the same way as in Example 1 to be quaternized. Moreover, in the same way as in Example 1, a base polymer film $B_1$ and a polymer film $B_2$ having quaternary ammonium groups were obtained. The content of tertiary amino groups of the base polymer film $B_1$ was 1.08 mmol/g and that of the polymer film $B_2$ having quaternary ammonium groups was 0.410 mmol/g, respectively. These results showed that the degree of quaternization was about 62%. Then, a heparinized polymer film $B_3$ having quaternary ammonium groups was obtained in the same way as in Example 1. Then, a relative coagulation time, activity of complement, a content of S (% by weight), and Na/S molar ratio were measured in the same way as in Example 1. The results are shown in Table 1.

Example 3

In the same way as in Example 1, a base polymer film $C_1$ was obtained from the base polymer solution B obtained in Example 2, i.e., the base polymer film $C_1$ is just the same as the base polymer film $B_1$. The base polymer solution B was treated with ethyl iodide to be quaternized in the same way as in Example 1, thereby obtaining a polymer film $C_2$ having quaternary ammonium groups. The content of tertiary amino groups of the base polymer film $C_1$ was 1.08 mmol/g and that of the polymer film $C_2$ having quaternary ammonium groups was 0.203 mmol/g. These results showed that the degree of quaternization was about 81%. This polymer film $C_2$ having quaternary ammonium groups was heparinized in the same way as in Example 1 to obtain a heparinized polymer film $C_3$ having quaternary ammonium groups. Then, a relative coagulation time, activity of complement, and a content of S (% by weight), and Na/S molar ratio were measured in the same as in Example 1. The results are shown in Table 1.

Comparative Example 1

In the same way as in Example 1, a base polymer film $D_1$ was obtained from the base polymer solution B obtained in Example 2, i.e., the base polymer film $D_1$ is just the same as the base polymer film $B_1$. The base polymer solution B was treated with hexyl iodide to be quaternized in the same way as in Example 1, thereby obtaining a polymer film $D_2$ having quaternary ammonium groups, i.e., the polymer film $D_2$ having quaternary ammonium groups is just the same as the polymer film $B_2$ having quaternary ammonium groups. The content of tertiary amino groups of the base polymer film $D_1$ was 1.08 mmol/g and that of the polymer film $D_2$ having quaternary ammonium groups was 0.410 mmol/g. These results showed that the degree of quaternization was about 62%. This polymer film $D_2$ having quaternary ammonium groups was heparinized with a 1% solution of heparin sodium salt (dimethyl-acetamide/water= 3/2 by weight was used as a solvent), thereby obtaining a heparinized polymer film $D_3$ having quaternary ammonium groups. Then, a relative coagulation time, activity of complement, and a content of S (% by weight), and Na/S molar ratio were measured in the same as in Example 1. The results are shown in Table 1.

Comparative Example 2

In the same way as in Example 1, a base polymer film $E_1$ was obtained from the base polymer solution B obtained in Example 2, and a polymer film $E_2$ having quaternary ammonium groups were obtained in the same way as in Example 1, i.e., the base polymer $E_1$ and the polymer film $E_2$ having quaternary ammonium groups are respectively the same as the base polymer film $B_1$ and the polymer film $B_2$ having quaternary ammonium groups. The content of tertiary amino groups of the base polymer film $E_1$ was 1.08 mmol/g, that of the polymer film $E_2$ having quaternary ammonium groups was 0.410 mmol/g, and the degree of quaternization was 62%. In the same way as in Example 1, this polymer film $E_2$ having quaternary ammonium groups was heparinized with a 1% solution of heparin sodium salt (water was used as a solvent) to obtain a heparinized polymer film $E_3$ having quaternary ammonium groups. Then a relative coagulation time, activity of complement, a content of S (% by weight), and Na/S molar ratio were measured in the same as in Example 1. The results are shown in Table 1.

As is apparent from the results of Table 1, in this stage, both heparinized polymer films having quaternary ammonium groups in Comparative Example 1 and Comparative Example 2 exhibited compatibility with blood comparable to those of Examples 1, 2, and 3.

Each of the heparinized polymer films $A_3$ to $E_3$ having quaternary ammonium groups was immersed in 200 ml of physiological saline and eluted for 2 weeks while changing physiological saline every day. The results obtained by measuring these eluted films for a relative coagulation time and a content of S after being eluted for 2 weeks in the heparinized polymer film having quaternary ammonium groups are shown in Table 2.

TABLE 2

| Immersion time (day) | Example 1 Relative coagulation time of Heparinized polymer film $A_3$ having quaternary ammonium groups | Example 2 Relative coagulation time of Heparinized polymer film $B_3$ having quaternary ammonium groups | Example 3 Relative coagulation time of Heparinized polymer film $C_3$ having quaternary ammonium groups | Comparative Example 1 Relative coagulation time of Heparinized polymer film $D_3$ having quaternary ammonium groups | Comparative Example 2 Relative coagulation time of Heparinized polymer film $E_3$ having quaternary ammonium groups |
|---|---|---|---|---|---|
| 1 | >10 | >10 | >10 | >10 | 7.0 |
| 3 | >10 | >10 | >10 | >10 | 3.2 |
| 5 | >10 | >10 | >10 | 7.0 | 2.8 |
| 7 | >10 | >10 | >10 | 4.8 | 2.8 |
| 10 | >10 | >10 | >10 | 4.8 | 2.8 |
| 14 | >10 | >10 | >10 | 3.0 | 2.8 |
| Content of S after the elution for 14 days (% by weight) | 0.970 | 1.01 | 1.02 | 0.251 | 0.104 |

From the results of Tables 1 and 2, as the value of the Na/S molar ratio became greater, the bond between the heparin and the polymer was weaker and the heparin was likely to be released. Therefore, the effects of the heparin were decreased as the immersion time became longer. After 2 hours, the effects of the heparin had completely disappeared.

From the above, it is apparent that the heparinized polymer films having quaternary ammonium groups of Examples 1, 2, and 3 possess satisfactory compatibility with blood for a long period to time.

Example 4

First, 1,800 parts of polydimethylsiloxanediol with a number average molecular weight of 1,800 represented by the following formula (V):

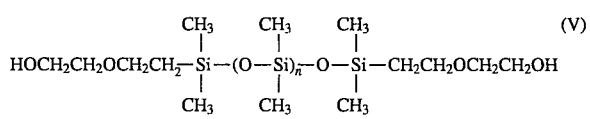

$$\text{HOCH}_2\text{CH}_2\text{OCH}_2\text{CH}_2-\underset{\underset{\text{CH}_3}{|}}{\overset{\overset{\text{CH}_3}{|}}{\text{Si}}}-(\text{O}-\underset{\underset{\text{CH}_3}{|}}{\overset{\overset{\text{CH}_3}{|}}{\text{Si}}})_n-\text{O}-\underset{\underset{\text{CH}_3}{|}}{\overset{\overset{\text{CH}_3}{|}}{\text{Si}}}-\text{CH}_2\text{CH}_2\text{OCH}_2\text{CH}_2\text{OH} \quad (V)$$

300 parts of the polyaminoetherdiol (a) of Example 1, 90.1 parts of 1,4-butanediol, 0.3 parts of dibutyltin dilaurate, and 554 parts of MDI were dissolved in a mixed solvent of 1,994 parts of THF and 3887 parts of DMF. The mixture was allowed to react under a stream of nitrogen at 40° C. for 1 hour and at 60° C. for another 15 hours, thereby obtaining a base polymer solution F having a solid content of 32% and a viscosity of 3,200 poises (30° C). In the same way as in Example 1, a base polymer film $F_1$ and a polymer film $F_2$ having quaternary ammonium groups were obtained by using this base polymer solution F. The content of tertiary amino groups of the base polymer film $F_1$ was 0.67 mmol/g and that of the polymer film $F_2$ having quaternary ammonium groups was 0.25 mmol/g. These results showed that the degree of quaternization was about 63%.

Next, the oxygen permeation coefficients of these films were measured by means of an apparatus for measuring gas permeation (Yanagimoto Co., Ltd.). The oxygen permeation coefficient of the base polymer film $F_1$ was $3.35 \times 10^{-8}$ cm$^3$ (STP) cm/cm$^2$·sec·cmHg, and that of the polymer film $F_2$ having quaternary ammonium groups was $3.78 \times 10^{-8}$ (hereinafter, the units "cm$^3$ (STP)·/cm$^2$·sec·cmHg" will be omitted).

Then, the polymer film $F_2$ having quaternary ammonium groups was treated with heparin by being immersed in a 1% solution of heparin sodium salt (THF/water=1/10 by weight was used as a solvent) at 60° C. for 2 hours, thereby obtaining heparinized polymer film $F_3$ having quaternary ammonium groups. The Na/S molar ratio of the heparinized polymer film $F_3$-having quaternary ammonium groups was 0.382. These resulting films were cut into circles with a diameter of 3 cm, and these samples were thoroughly rinsed with distilled water and dried by blotting up water on the film surfaces with filter paper. The film samples were measured for a relative coagulation time in the same way as in Example 1. The results are shown in Table 3.

Moreover, activity of the complement was measured in the same way as in Example 1. The results are shown in Table 3.

Moreover, each of the resulting films was thoroughly dried and weighed, then immersed in distilled water at 20° C. for 24 hours. After that the surface of each film was wiped and weighed. A coefficient of water absorption was determined from the weight before and after being immersed. The calculation of the coefficient of water absorption was conducted by using following equation:

$$\text{Coefficient of water absorption (\%)} = \{(W-D)/D\} \times 100$$

In this equation, W is a film weight after being immersed, and D is a film weight before being immersed. The results are shown in Table 3. The unit of the oxygen permeation coefficients is cm$^3$ (STP)·cm/(cm$^2$·sec·cmHg).

TABLE 3

|  |  | Coefficient of Oxygen permeability ($\times 10^{-8}$) | Relative coagulation time (glass = 1.00) | Activity of Complement $CH_{50}$ (%) | C3a (ng/ml) | C5a (ng/ml) | Coefficient of water absorption (%) | Na/S Molar ratio |
|---|---|---|---|---|---|---|---|---|
| Example 4 | Base polymer film $F_1$ | 3.35 | 3.00 | 94.0 | 350 | 200 | 0.12 | — |
|  | Polymer film $F_2$ having quaternary ammonium groups | 3.78 | 3.45 | 100 | 200 | 120 | 1.20 | — |
|  | Heparinized polymer film $F_3$ having quaternary ammonium groups | 3.65 | >10 | 100 | 20 | 40 | 1.33 | 0.382 |
| Example 5 | Base polymer film $G_1$ | 3.07 | 2.78 | 95.0 | 345 | 180 | 0.15 | — |
|  | Polymer film $G_2$ having quaternary ammonium groups | 3.12 | 3.11 | 99.0 | 195 | 132 | 0.76 | — |
|  | Heparinized polymer film $G_3$ having quaternary ammonium groups | 3.00 | >10 | 99.0 | 25 | 38 | 0.42 | 0.379 |
| Example 6 | Base polymer film $H_1$ | 3.00 | 2.50 | 93.0 | 360 | 210 | 0.11 | — |
|  | Polymer film $H_2$ having quaternary ammonium groups | 2.95 | 2.77 | 100 | 210 | 135 | 0.53 | — |
|  | Heparinized polymer film $H_3$ having quaternary ammonium groups | 3.10 | >10 | 100 | 23 | 43 | 0.56 | 0.369 |
| Comparative Example 3 | Base polymer film $I_1$ | 3.07 | 2.78 | 95.0 | 345 | 180 | 0.15 | — |
|  | Polymer film $I_2$ having quaternary ammonium groups | 2.97 | 2.50 | 98.0 | 220 | 150 | 7.17 | — |
|  | Heparinized polymer film $I_3$ having quaternary ammonium groups | 2.88 | >10 | 100 | 35 | 60 | 14.31 | 0.624 |
| Comparative | Base polymer film $J_1$ | <0.1 | 2.00 | 60.0 | 600 | 450 | 63.0 | — |

TABLE 3-continued

|  |  | Coefficient of Oxygen permeability ($\times 10^{-8}$) | Relative coagulation time (glass = 1.00) | Activity of Complement | | | Coefficient of water absorption (%) | Na/S Molar ratio |
|---|---|---|---|---|---|---|---|---|
|  |  |  |  | $CH_{50}$ (%) | C3a (ng/ml) | C5a (ng/ml) |  |  |
| Example 4 | Polymer film $J_2$ having quaternary ammonium groups | <0.1 | 1.57 | 55.0 | 750 | 450 | 90.0 | — |
|  | Heparinized polymer film $J_3$ having quaternary ammonium groups | <0.1 | >10 | 75.0 | 300 | 200 | 90.0 | 0.712 |

Example 5

First, 3,240 parts of polydimethysiloxanediol represented by the formula (V) with a number average molecular weight of 2,040, 1,195 parts of MDI, 773.4 parts of the polyaminoetherpolyol (b), 0.3 parts of dibutyltin dilaurate, and 191.1 parts of 1,4-butanediol were dissolved in a mixed solvent of 3,782 parts of THF and 7,564 parts of DMF. The mixture was allowed to react at 20° C. under a stream of nitrogen for 1 hour and at 40° C. for 20 hours, thereby obtaining a base polymer solution G having a solid content of 32% and a viscosity of 1800 poises (30° C.). This base polymer solution G was treated in the same way as in Example 1 to obtain a base polymer film $G_1$ and a polymer film $G_2$ having quaternary ammonium groups. The content of tertiary amino groups of the base polymer film $G_1$ was 1.08 mmol/g and that of the base polymer film $G_2$ having quaternary ammonium groups was 0.410 mmol/g. These results showed that the degree of quaternization was about 62%. Then, a heparinized polymer film $G_3$ having quaternary ammonium groups was obtained by heparinizing the polymer film $G_2$ having quaternary ammonium groups (the Na/S molar ratio was 0.379) in the same way as in Example 4. Then, a coefficient of oxygen permeability, a relative coagulation time, activity of complement, and a coefficient of water absorption were measured in the same way as in Example 4. The results are shown in Table 3.

Example 6

First, 8,738 parts of 3-n-butyl-3-aza-1,5-pentanediol and 10.3 parts of phosphorous acid were charged into an autoclave. The mixture was heated and stirred at a temperature of 200° to 230° C. at a constant. pressure under a stream of nitrogen for 26 hours and allowed to react while distilling off generated water. Then, the mixture was depressurized at 230° C. from 760 mmHg to 0.3 mmHg over 2 hours and was allowed to react at 230° C. and 0.3 mmHg for another 3 hours. As described above, polyaminoetherdiol (c) having an OH valence of 58.7 and containing 6.30mmol/g of nitrogen atoms of the tertiary amino groups was obtained.

Next, 3,240 parts of polydimethylsiloxanediol with a number average molecular weight of 2,040 represented by the formula (V), 1,195 parts of MDI, 827.3 parts of the polyaminoetherdiol (c), 0.3 parts of dibutyltin dilaurate, and 191.1 parts of 1,4-butanediol were dissolved in a mixed solvent of 3,802 parts of THF and 7,604 parts of DMF. The mixture was allowed to react at 20° C. under a stream of nitrogen for 1 hour and then at 40° C. for another 20 hours. As described above, a base polymer solution H having a solid content of 32% and a viscosity of 1,830 poises (30° C.) was obtained. This base polymer solution H was treated in the same way as in Example 1, thereby obtaining a base polymer film $H_1$ and a polymer film $H_2$ having quaternary ammonium groups. The content of tertiary amino groups of the base polymer film $H_1$ was 1.08 mmol/g and that of the polymer film $H_2$ having quaternary ammonium groups was 0.410 mmol/g. These results showed that the degree of quaternization was about 62%. Then, in the same way as in Example 4, a heparinized polymer film $H_3$ having quaternary ammonium groups was obtained by heparinizing the polymer film $H_2$ having quaternary ammonium groups (the Na/S molar ratio was 0.369). Then, a coefficient of oxygen permeability, a relative coagulation time, activity of complement, and a coefficient of water absorption were measured in the same way as in Example 4. The results are shown in Table 3.

Comparative Example 3

A base polymer film 11 was obtained in the same way was in Example 1 from the base polymer solution G obtained in Example 5, i.e., the base polymer film $I_1$ is just the same as the base polymer film $G_1$. The base polymer solution G was treated with ethyl iodide to be quaternized in the same way as in Example 1, thereby obtaining a polymer film $I_2$ having quaternary ammonium groups. The content of tertiary amino groups of the base polymer film $I_1$ was 1.08 mmol/g and that of the polymer film $I_2$ having quaternary ammonium groups was 0.210 mmol/g. These results showed that the degree of quaternization was about 82%. Then, in the same way as in Example 4, a heparinized polymer film $I_3$ was obtained by heparinizing the polymer film $I_2$ having quaternary ammonium groups (the Na/S molar ratio was 0.624). Then, a coefficient of oxygen permeability, a relative coagulation time, activity of complement, and a coefficient of water absorption were measured in the same way as in Example 4. The results are shown in Table 3.

Comparative Example 4

First, 24 parts of acrylonitrile, 89 parts of acrylamide, and 126 parts of dimethylsulfoxide were thoroughly mixed. To this mixture, 0.2 parts of dodecylmercaptan as a chain transfer agent and 0.3 parts of bromoform as a polymerization initiator were added. The mixture was photo-polymerized by irradiating light with a high-voltage mercury lamp of 100 W at a distance of 10 cm for 7 hours. The resulting photo-polymerized solution was poured into a great amount of methanol, and precipitated and coagulated, thereby obtaining 24.4 parts of a polymer. Ten g of this polymer was dissolved in 120 parts of dimethylsulfoxide, to which 5.0 parts of dimethylaminoethylmethacrylate was added. This mixture was photo-grafted by irradiating light with a high-voltage mercury lamp of 100 W at a distance of 10 cm for 19 hours. The resulting photo-grafted solution was poured into methanol, and precipitated and coagulated, thereby obtaining 12.8 parts of graft polymer. Then, the graft polymer was molded in the same way as in Example 4 to obtain a base polymer film $J_1$. The resulting graft polymer was dissolved in dimethylformamide, to which ethyl bromide was added to be quaternized. Then, the mixture was molded into a polymer film $J_2$ having quaternary ammonium groups. In the same way as in Example 4, this polymer film $J_2$ having quaternary ammonium groups was heparinized to obtain a heparinized polymer film $J_3$ having quaternary ammonium groups (the Na/S molar ratio was 0.712).

Next, a coefficient of oxygen permeability, a relative coagulation time, activity of complement, and a coefficient of water absorption were measured in the same was as in Example 4. The results are shown in Table 3.

As is apparent from Table 3, the heparinized polymer film $J_3$ having quaternary ammonium groups of Comparative Example 4, which does not contain polydimethylsiloxane units is poor in gas-permeability and activates the complement. In contrast, the heparinized polymer films having quaternary ammonium groups of Examples 4 to 6 possessed satisfactory gas-permeability, the activity of complement being suppressed. In this stage, the heparinized polymer films 13 having quaternary ammonium groups of Comparative Example 3 possessed properties comparable to those of Examples 4 to 6.

The heparinized polymer films $F_3$ to $J_3$ having quaternary ammonium groups obtained in Examples 4 to 6 and Comparative Examples 3 and 4 were immersed in 200 ml of physiological saline and eluted for 2 weeks while changing physiological saline every day. The results obtained by measuring a relative coagulation time of these eluted film are shown in Table 4.

As described above, it is apparent that the heparinized polymer films having quaternary ammonium groups of Examples 4, 5, and 6 have satisfactory gas-permeability and are compatible with blood for a long period of time.

As is apparent from the above description, according to the present invention, the material compatible with blood having a great amount of bonded heparins can be provided. Thus, a high compatibility with blood can be obtained without using the heparin together while the blood is circulating in vivo, and moreover, the compatibility with blood can be maintained for a long period of time. Furthermore, the material has a satisfactory mechanical property such as elasticity, and even when it is brought into contact with body fluid such as blood, harmful eluted substances are hardly generated.

Because of the above-mentioned advantages, the material compatible with blood of the present invention can be widely applicable to various kinds of apparatuses or equipment for medical use. More specifically, the material can be used as sheets, tubes, or hollow fibers for blood dialysis of renal failure patients; and as coating materials for adsorbing egesta in the blood. In addition to such an artificial kidney, the material can be used as film materials for an artificial lung (partition wall between the blood and the oxygen) and sheet materials of a sheet lung for an artificial heart-lung machine. Moreover, the material can be widely used as aortic balloons, artificial blood vessels, blood bags, catheters, cannulas, shunts, blood circuits, and coating materials used for these.

It is understood that various other modifications will be apparent to and can be readily made by those skilled in the art without departing from the scope and spirit of this invention. Accordingly, it is not intended that the scope of the claims appended hereto be limited to description as set forth herein, but rather that the claims be construed as encompassing all the features of patentable novelty that

TABLE 4

| Immersion time (day) | Example 4 Relative coagulation time of Heparinized polymer film $F_3$ having quaternary ammonium groups | Example 5 Relative coagulation time of Heparinized polymer film $G_3$ having quaternary ammonium groups | Example 6 Relative coagulation time of Heparinized polymer film $H_3$ having quaternary ammonium groups | Comparative Example 3 Relative coagulation time of Heparinized polymer film $I_3$ having quaternary ammonium groups | Comparative Example 4 Relative coagulation time of Heparinized polymer film $J_3$ having quaternary ammonium groups |
| --- | --- | --- | --- | --- | --- |
| 1 | >10 | >10 | >10 | 7.0 | 3.5 |
| 3 | >10 | >10 | >10 | 2.8 | 2.0 |
| 5 | >10 | >10 | >10 | 2.8 | 2.0 |
| 7 | >10 | >10 | >10 | 2.8 | 2.0 |
| 10 | >10 | >10 | >10 | 2.8 | 2.0 |
| 14 | >10 | >10 | >10 | 2.8 | 2.0 |

Table 4 presents data regarding the heparinized polymer films having quaternary ammonium groups of Examples 4 to 6, which have a coefficient of water absorption of 6% or less, as indicated therein; these films possessed satisfactory compatibility with blood even after the elution in the physiological saline for 2 weeks. In contrast, in the heparinized polymer films having quaternary ammonium groups of Comparative Examples 3 and 4, which have a great coefficient of water absorption, the heparin was rapidly eluted, so that the effects of the heparin disappeared.

reside in the present invention, including all features that would be treated as equivalents thereof by those skilled in the art to which this invention pertains.

What is claimed is:

1. A composition compatible with blood prepared by ion exchange complexation of a polymer having quaternary ammonium groups with an alkali metal salt of a polyanion selected from the group consisting of heparin, chondroitin sulfate, dextran sulfate, and polyvinyl alcohol sulfate, wherein said polymer having quaternary ammonium groups is prepared by quaternizing a polymer containing tertiary amino groups with a quaternizing agent, and wherein the equivalent ratio, M/S, of alkali metal atoms (M) to sulfur atoms (S) in the composition is 0.4 or less.

2. A composition compatible with blood according to claim 1, wherein the polymer having quaternary ammonium groups is a polyurethane or polyurethaneurea having quaternary ammonium groups obtained by quaternizing the tertiary amino groups of a polyurethane or polyurethaneurea, wherein the polyurethane or the polyurethaneurea is obtained by reacting a polyaminoetherpolyol that has at least two functional groups that react with isocyanato groups with a polyisocyanate, and wherein the polyaminoetherpolyol is obtained by condensation of diols containing at least 30 mol % amino alcohol represented by a structure selected from the group consisting of

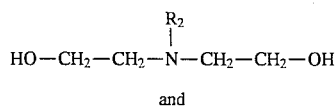

and

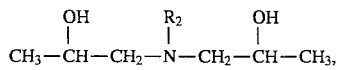

wherein $R_2$ is an alkyl group having 1 to 15 carbon atoms.

3. A composition compatible with blood according to claim 1, wherein the polymer having quaternary ammonium groups is a polyurethane or polyurethaneurea having quaternary ammonium groups obtained by quaternizing at least a part of the tertiary amino groups in a polyurethane or polyurethaneurea with an alkyl halide or an active ester, wherein the polyurethane or the polyurethaneurea is prepared by reacting a diisocyanate, a polysiloxane having a hydroxyl group or an amino group at one or more of its molecular termini, and a polyaminoetherpolyol having tertiary amino groups.

4. A composition compatible with blood according to claim 1, wherein the polymer having quaternary ammonium groups contains either a polyurethane or a polyurethaneurea having quaternary ammonium groups, and a polytetramethylene glycol.

5. A composition compatible with blood according to claim 2, wherein the total number of carbon atoms of two side chains bonded to a quaternary nitrogen atom of a polymer having quaternary ammonium groups is 5 to 16, in which one chain is bonded to a tertiary nitrogen atom of the polymer having tertiary amino groups and the other side chain is derived from the quaternizing agent.

6. A composition compatible with blood according to claim 1, wherein the ion exchange complexation is carried out in a mixed solvent of a water-soluble organic solvent and water.

7. A composition compatible with blood obtained by ion exchange complexation of a polymer having quaternary ammonium groups with an alkali metal salt of a polyanion selected from the group consisting of heparin, chondroitin sulfate, dextran sulfate, and polyvinyl alcohol sulfate, wherein the polymer is a polyurethane or a polyurethaneurea obtained by quaternizing at least a part of the tertiary amino groups in the polymer with an alkyl halide having 1 to 10 carbon atoms, wherein the polyurethane or the polyurethaneurea is obtained by reacting a polyaminoetherpolyol that has at least two functional groups that react with isocyanato groups with a polyisocyanate, and wherein the polyaminoetherpolyol contains, as a diol component, at least 30 mol % of an amino alcohol represented by the structure

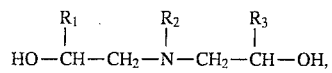

wherein $R_1$ and $R_3$ are independently alkyl groups with 1 to 5 carbon atoms, and $R_2$ is an alkyl groups with 1 to 15 carbon atoms, an aralkyl group with 7 to 15 carbon atoms, or an aryl group with 6 to 15 carbon atoms, wherein the total number of carbon atoms of two side chains bonded to a quaternary nitrogen atom of a polymer having quaternary ammonium groups is 5 to 16, in which one chain is bonded to a tertiary nitrogen atom of the polymer having tertiary amino groups and the other side chain is derived from the quaternizing agent, and wherein the equivalent ratio, M/S, of alkali metal atoms (H) to sulfur atoms (S) in the composition is 0.4 or less.

8. A composition compatible with blood according to claim 7, wherein the alkyl halide has 2 to 8 carbon atoms.

9. A composition compatible with blood according to claim 7, wherein the total number of carbon atoms of said two side chains bonded to a quaternary nitrogen atom of a polymer having quaternary ammonium groups is 6 to 14.

10. A composition compatible with blood according to claim 7, wherein the polyaminoetherpolyol has a molecular weight of from 200 to 8,000.

11. A composition compatible with blood according to claim 7, wherein the polyaminoetherpolyol has a molecular weight of from 500 to 4,000.

12. A composition compatible with blood according to claim 7, wherein the tertiary amino groups of the polyaminoetherpolyol precursor of the polyurethane or the polyurethaneurea are present in an amount of 0.05 to 5.00 mmol/g.

13. A composition compatible with blood according to claim 7, wherein the tertiary amino groups of the polyaminoetherpolyol precursor of the polyurethane or the polyurethaneurea are present in an amount of 0.1 to 3.0 mmol/g.

14. A composition compatible with blood according to claim 7, wherein 10% or more of the tertiary amino groups are quaternized.

15. A composition compatible with blood according to claim 7, wherein 20% or more of the tertiary amino groups are quaternized.

16. A composition compatible with blood according to claim 7, wherein the alkali metal salt of heparin is selected from the group consisting of a sodium salt of heparin and a potassium salt of heparin.

17. A composition compatible with blood according to claim 7, wherein the ion exchange complexation is carried out in a mixed solvent of a water-soluble organic solvent and water.

18. A composition compatible with blood according to claim 17, wherein the water-soluble organic solvent is tetrahydrofuran, and the ratio of the water to the tetrahydrofuran is from 20/1 to 3/7.

19. A composition compatible with blood according to claim 18, wherein the ratio of the water to the tetrahydrofuran is from 10/1 to 3/5.

20. A composition compatible with blood according to claim 1, wherein the polymer having quaternary ammonium groups is a film.

21. A composition compatible with blood according to claim 7, wherein the polymer having quaternary ammonium groups is a film.

* * * * *

UNITED STATES PATENT AND TRADEMARK OFFICE
CERTIFICATE OF CORRECTION

PATENT NO. : 5,541,305
DATED : July 30, 1996
INVENTOR(S) : Yokota et al.

It is certified that error appears in the above-identified patent and that said Letters Patent is hereby corrected as shown below:

In Column 9, line 24: "for i hour" should read --for 1 hour--.

In Column 10, line 52: "of c3a and" should read --of C3a and--.

In Column 18, line 35: "11" should read --$I_1$--.

In Column 20, line 12: "the:" should read --the--.

In Claim 7, Column 22, line 20: "(H)" should read --(M)--.

Signed and Sealed this

Fourteenth Day of January, 1997

Attest:

BRUCE LEHMAN

Attesting Officer    Commissioner of Patents and Trademarks